United States Patent [19]

White et al.

[11] 4,017,423
[45] Apr. 12, 1977

[54] PROCESS FOR THE PREPARATION OF UNSATURATED ACIDS FROM UNSATURATED ALDEHYDES

[75] Inventors: James F. White, Akron; James R. Rege, Lakewood, both of Ohio

[73] Assignee: The Standard Oil Company (Ohio), Cleveland, Ohio

[22] Filed: Aug. 18, 1975

[21] Appl. No.: 605,362

[52] U.S. Cl. .............................. 252/437; 252/435; 260/530 N
[51] Int. Cl.$^2$ ......................................... B01J 27/14
[58] Field of Search ............................ 252/435, 437

[56] References Cited

UNITED STATES PATENTS

| | | | |
|---|---|---|---|
| 3,086,026 | 4/1963 | Wiebusch et al. | 252/435 X |
| 3,156,705 | 11/1964 | Kerr | 252/435 X |
| 3,795,703 | 3/1974 | Niin et al. | 252/435 X |
| 3,882,047 | 5/1975 | Niina et al. | 252/435 |
| 3,893,945 | 7/1975 | Kobayashi et al. | 252/435 |

OTHER PUBLICATIONS

Derwent Abstracts of DT2455–216 as cited by Applicants.
Derwent Abstracts of DT2454–587 as cited by Applicants.

*Primary Examiner*—Patrick P. Garvin
*Assistant Examiner*—William G. Wright
*Attorney, Agent, or Firm*—Herbert D. Knudsen; Larry W. Evans; Gwenetta D. Hill

[57] ABSTRACT

Catalysts containing the oxides of molybdenum and phosphorus promoted with rubidium and at least one element selected from the group consisting of As, Cd, In, Sn, Tl, K, Ca, V, U, Ce, W, Ni, Zr, Ba, Fe, Rh, Mn, Re, Ru, Co, and Cu have been found to be especially desirable in the vapor phase oxidation of acrolein and methacrolein with molecular oxygen to yield acrylic acid and methacrylic acid respectively. The reaction of methacrolein gives an especially pure product in high yields and selectivities of methacrylic acid.

8 Claims, No Drawings

PROCESS FOR THE PREPARATION OF UNSATURATED ACIDS FROM UNSATURATED ALDEHYDES

BACKGROUND OF THE INVENTION

Japanese Pat. No. 4,733,082 discloses catalysts containing the oxides of molybdenum, phosphorus, and at least one element selected from the group consisting of arsenic, boron, silicon, cadmium, lead, tungsten, thallium, indium, germanium, and tin for the oxidation of unsaturated aldehydes to unsaturated acids, and preferredly for the oxidation of methacrylaldehyde to methacrylic acid. U.S. Pat. No. 3,875,220 discloses desirable catalysts containing phosphorus, vanadium, and molybdenum for the oxidation of methacrolein with molecular oxygen to obtain methacrylic acid. These catalysts may be optionally promoted with bismuth, arsenic, boron, cerium, chromium, silver, iron, tungsten, lead, manganese, thallium, tellerium, nickel, niobium, boron, tin and/or copper. German Pat. No. 2,048,602 discloses catalysts containing molybdenum, phosphorus, and elements such as tungsten, arsenic indium, and cadmium. The present invention is a result of a search for more efficient and desirable catalysts for the production of acrylic acid and methacrylic acid. Unexpected higher yields and selectivities of acrylic acid and methacrylic acid are obtained by the vapor phase oxidation of acrolein and methacrolein, respectively, with molecular oxygen in the presence of the new and useful catalysts of the present invention.

SUMMARY OF THE INVENTION

It has now been discovered according to the present invention in the process for the production of acrylic acid and methacrylic acid by the oxidation of acrolein and methacrolein respectively, with molecular oxygen in the vapor phase at a reaction temperature of about 200° to about 500° C in the presence of catalyst, and optionally in the presence of steam, the improvement which comprises using as a catalyst a catalyst described by the formula $$A_aRb_bMo_3P_cO_x$$

wherein A is at least one element selected from the group consisting of arsenic, cadmium, indium, tin, thallium, potassium, calcium, vanadium, uranium, cerium, tungsten, nickel, zirconium, barium, iron, rhodium, tin, manganese, rhenium, ruthenium, cobalt, and copper.
and wherein
$a$ is a positive number less than about 20;
$b$ is about 0.01 to about 3;
$c$ is a positive number less than about 2;
$x$ is the number of oxygens required by the valence states of the other elements present.

The suprisingly advantageous catalysts of this invention give improved yields of acrylic acid and methacrylic acid when compared to the art catalysts. Especially high yields and selectivities of methacrylic acid are obtained from methacrolein in an efficient, convenient, and economical manner at a relatively low temperature. The exortherm of the reaction is low, thereby, allowing easy reaction control.

The most significant aspect of the present invention is the catalyst employed. The catalyst may be any of the catalysts delineated by the above formula. Preferred catalysts within the formula are described wherein A is at least one element selected from the group consisting of arsenic, cadmium, indium, thallium and tin. Catalysts containing the oxides of molybdenum, phosphorus, and at least one element such as arsenic, cadmium, indium, thallium and tin are known for the vapor phase oxidation of unsaturated aldehydes to unsaturated acids, and preferrably for the oxidation of methacrylaldehyde to methacrylic acid. Catalysts containing molybdenum, phosphorus, and elements such as tungsten, arsenic, indium, and cadmium have also been disclosed. Catalysts of special interest in this invention are described wherein A is at least one element selected from the group consisting of K, Ca, V, U, Ce, W, Ni, Zr, Ba, Fe, Rh, Sn, Mn, Re, Ru, Co, and Cu. Catalysts containing phosphorus, vanadium, and molybdenum and optionally promoted with elements such as As, Ce, Fe, W, Mn, C, Ni, Sn, and/or Cu are known. However, unexpected improvements are achieved in yields of acrylic acid and methacrylic acid by the use of the catalysts of the present invention, as compared to results obtained with the art catalysts containing no rubidium.

Superior results are obtained when $a$ is a positive number less than about 12; $b$ is about 0.01 to about 1.0 and $c$ is about 0.01 to about 0.75.

The methods of preparing the catalysts of the present invention may vary widely. A number of techniques are known to those skilled in the art. Methods of catalyst preparations such as coprecipation, evaporative drying, or oxide mixing, followed by calcining the resulting catalysts may be successfully employed.

The preferred precedure of this invention involves the preparation of the catalysts in an aqueous slurry or solution of molybdenum, phosphorus, and the remaining components; evaporation of this aqueous mixture; and calcination of the resulting catalysts. Suitable molybdenum compounds that may be employed in the preparation of the catalysts delineated by the above formula include molybdenum trioxide, phosphomobybdic acid, molybdic acid, ammonium heptamolybdate, and the like. Suitable phosphorus compounds that may be employed in the preparation of the catalysts include orthophosphoric acid, metaphosphoric acid, triphosphoric acid, phosphorus pentabromide, phosphorus pentachloride, and the like. The remaining components of the catalysts may be added as oxide, acetate, formate, sulfate, nitrate carbonate, and the like.

The catalysts of this invention also may be prepared by mixing the catalytic components in an aqueous slurry or solution, heating the aqueous mixture to dryness; and calcining the resulting catalysts.

The best results are obtained by refluxing phosphoric acid and molybdenum trioxide in water for about 1.5 to 3 hours; adding a rubidium salt; followed by adding the remaining components to the aqueous slurry and boiling to a thick paste, drying at 110° to 120° C in air; and calcining the resulting catalysts. Excellent results are achieved when soluble salts of the catalytic components other than molybdenum are employed in the catalyst preparations. Insoluble salts or oxides may be used, however, optimum results are achieved when soluble salts other than molybdenum and phosphorus are used in the preparation of the catalysts.

The reactants of the reaction of the invention are acrolein or methacrolein and molecular oxygen. Molecular oxygen is normally supplied to the reaction in the form of air, but oxygen gas could also be employed.

About 0.5 to about 10 moles of oxygen are normally added per mole of acrolein or methacrolein.

Optionally added to the reactants is steam or an inert diluent. Preferred reactions are conducted in the presence of substantial quantitites of steam in the range of about 2 to about 20 moles of steam per mole of acrolein or methacrolein.

The reaction temperature may vary as different catalysts are employed. Normally, temperatures of about 200° to about 500° C are employed with temperatures of about 250° to about 400° C being preferred.

The reaction may be conveniently conducted in either a fixed-bed or fluid-bed reactor. The contact time may be as low as a fraction of a second or as high as 20 seconds or more, the preferred contact time is 4 to 5 seconds. The reaction may be conducted at atmospheric, superatmospheric or subatmospheric pressure, with absolute pressures of about 0.5 to about 4 atmospheres being preferred.

When used in the reactor, the catalyst may be in a supported or unsupported form. Suitable support materials include silica, Alundum, alumina, boron phosphate, zirconia, titanium and the like, but the most preferred is zirconia.

The examples below are representative of the catalysts that are suitable for the process of the invention, however, the scope of the invention is not limited to these examples. The preferred reaction of the invention is the oxidation of methacrolein to methacrylic acid. Of course, acrolein can be converted to acrylic acid using the catalysts and techniques of the present invention.

SPECIFIC EMBODIMENTS

Examples 1 to 35

Preparation of Various Catalysts of the Invention

Example 1

A catalyst of the formula $In_{0.05}Rb_{0.5}Mo_3P_{.33}O_x$ was prepared as follows:

A slurry was prepared of 86.2 g (0.6 mole) of molybdenum trioxide and 7.7 g. (0.67 mole P) of 85% phosphoric acid in 1500 mls. of distilled water; boiled with stirring for 2 hours to form phosphomolybdic acid which was greenish yellow in color. 2.3 g. (0.01 mole) of indium acetate was added to the slurry; no change in color, followed by the addition of 14.4 g. (0.1 mole) of rubidium acetate. The aqueous mixture which was yellow in color and was boiled to dryness; dried overnight at 110° C in air. The catalyst was ground and screened to 20/30 mesh fraction.

Examples 2 to 20

Various catalysts of the present invention were prepared. The catalysts were prepared according to the procedure of Example 1 using 86.2 g. of molybdenum trioxide, 7.7 g. of 85% phosphoric acid, and 14.4 g. of rubidium acetate. These catalysts have the general formula $A_{0.05}Rb_{0.5}Mo_3P_{.33}O_x$. The catalytic component, A, was added following the 2 hour-reflux of molybdenum trioxide and 85% phosphoric acid. To prepare the catalysts, the following compounds and amounts were used:

| Element | Compound | Amount, g. |
|---|---|---|
| Ni | Nickel oxide | 0.75 |
| V | Vanadium pentoxide | 0.91 |
| Cd | Cadium acetate | 2.7 |
| U | Uranyl acetate | 4.25 |
| As | Arsenic trioxide | 1.00 |
| Sn | Tin dioxide | 1.5 |
| Tl | Thallous Acetate | 2.63 |
| K | Potassium acetate | 1.0 |
| Ca | Calcium acetate hydrate | 1.26 |
| Ce | Cerium triacetate hydrate | 3.44 |
| W | Ammonium tungstate | 2.7 |
| Zr | Zirconyl acetate | 2.25 |
| Ba | Barium hydroxide | 1.7 |
| Fe | Ferric oxide | 0.77 |
| Rh | Rhodium trichloride hydrate | 2.63 |
| Mn | Manganese dioxide | 0.88 |
| Re | Rhenium heptoxide | 2.42 |
| Ru | Ruthenium trichloridehydrate | 2.73 |
| Co | Cobaltacetate hydrate | 2.5 |

The catalysts were boiled and dried according to Example 1. The catalysts were ground and screened to 20/30 mesh size.

Examples 21 to 33

Preparation of catalysts of the formula $A_{0.05}Rb_{0.5}Mo_3P_{.33}O_x$ wherein A includes at least two elements. The catalysts were prepared in the same manner as described in Example 1. The catalytic components of A were added following the 2 hour-reflux and addition of 85% phosphoric acid. To prepare the catalysts, the following compounds and amounts were used:

| A | Compounds | Amount, g. |
|---|---|---|
| $Fe_{0.025}Sn_{0.025}$ | Ferric oxide | 0.39 |
| | Tin dioxide | 0.75 |
| $Fe_{0.025}Mn_{0.025}$ | Ferric oxide | 0.39 |
| | Manganese dioxide | 0.43 |
| $Fe_{.1}Sn_{.1}$ | Ferric oxide | 1.56 |
| | Tin dioxide | 3.0 |
| $Fe_{.1}Mn_{.1}$ | Ferric oxide | 1.56 |
| | Manganese dioxide | 1.72 |
| $Fe_{.1}Ni_{.1}$ | Ferric oxide | 1.56 |
| | Nickel trioxide | 1.65 |
| $Fe_{.25}Mn_{.25}$ | Ferric oxide | 4.0 |
| | Manganese dioxide | 4.35 |
| $Sn_{.25}Mn_{.25}$ | Tin dioxide | 7.54 |
| | Manganese dioxide | 4.35 |
| $Co_{.025}Fe_{0.025}$ | Cobaltacetate hydrate | 1.25 |
| | Ferric oxide | 0.39 |
| $Fe_{0.015}Sn_{0.035}$ | Ferric oxide | 0.23 |
| | Tin dioxide | 1.05 |
| $Fe_{0.035}Sn_{0.015}$ | Ferric oxide | 0.54 |
| | Tin dioxide | 0.45 |
| $Sn_{0.025}Ni_{0.025}$ | Tin dioxide | 0.75 |
| | Nickel trioxide | 0.41 |
| $Fe_{0.025}Mn_{0.025}$ | Ferric oxide | 0.39 |
| | Manganese dioxide | 0.44 |
| $Sn_{0.025}$ | Tin dioxide | 0.75 |
| $Sn_{.125}Cu_{0.5}$ | Tin dioxide | 3.75 |
| | Copper acetate hydrate | 20.0 |

Examples 34 to 103

Preparation of Methacrylic Acid Using Various Catalysts of the Invention

The catalysts were prepared in the same manner as shown above using the appropriate ratio of ingredients. A portion of these catalyst particles were charged to a 20 cc. fixed-bed reactor consisting of a length of 1.3 cm. stainless steel tubing equipped with a full length 0.3 cm. axial thermowell. The reactor was heated to reaction temperature under a flow of air and a feed of methacrolein/air/steam of 1/6.2/5.2 was fed over the catalyst at an apparent contact time of 4.5 to 5 seconds. The reactor was run under the reaction conditions for 1 to 5 hours and the product was collected by scrubbing the reaction off gases in two series water scrubbers. The scrubber contents were combined and diluted to 1100 cc. for analysis and filtration for acid content. The scrubbed fixed gases were dried and analyzed on a conventional Houdry split column system.

The results are stated in terms as follows

Single Pass Yield = $\frac{\text{Moles of Methacrylic Acid Recovered}}{\text{Moles of Methacrolein in the feed}} \times 100$ Total Conversion = $\frac{\text{Moles of Methacrolein Reacted}}{\text{Moles of Methacrolein in the feed}} \times 100$ Selectivity = $\frac{\text{Single Pass Yield}}{\text{Total Conversion}} \times 100$ The experimental results are shown in the Table below.

TABLE

PREPARATION OF METHACRYLIC ACID USING VARIOUS CATALYSTS OF THE INVENTION

Examples 34 to 103.

| Example | Catalyst | Reaction Temp. °C | Total Conversion | Single Pass Yield | Selectivity |
|---|---|---|---|---|---|
| 34 | $In_{0.05}Rb_{0.5}Mo_3P_{.33}O_x$ | 343 | 85.5 | 62.0 | 71.3 |
| 35 | $In_{0.05}Rb_{0.5}Mo_3P_{.33}O_x$ | 357 | 93.5 | 65.5 | 70.5 |
| 36 | $Ni_{0.05}Rb_{0.5}Mo_3P_{.33}O_x$ | 343 | 90.0 | 67.0 | 68 |
| 37 | $Ni_{0.05}Rb_{0.5}Mo_3P_{.33}O_x$ | 357 | 90.7 | 66.7 | 72.3 |
| 38 | $U_{0.05}Rb_{0.5}Mo_3P_{.33}O_x$ | 343 | 90.4 | 64.0 | 67.3 |
| 39 | $U_{0.05}Rb_{0.5}Mo_3P_{.33}O_x$ | 357 | 90.0 | 62.0 | 66.4 |
| 40 | $Cd_{0.05}Rb_{0.5}Mo_3P_{.33}O_x$ | 343 | 90.0 | 58.2 | 64.7 |
| 41 | $As_{0.05}Rb_{0.5}Mo_3P_{.33}O_x$ | 343 | 72.3 | 52.0 | 70.1 |
| 42 | $As_{0.05}Rb_{0.5}Mo_3P_{.33}O_x$ | 371 | 88.4 | 62.8 | 72.3 |
| 43 | $Sn_{0.05}Rb_{0.5}Mo_3P_{.33}O_x$ | 343 | 92.1 | 62.8 | 65.6 |
| 44 | $Sn_{0.05}Rb_{0.5}Mo_3P_{.33}O_x$ | 329 | 92.0 | 62.5 | 65.5 |
| 45 | $Sn_{0.05}Rb_{0.5}Mo_3P_{.33}O_x$ | 316 | 87.5 | 60.0 | 68.0 |
| 46 | $Tl_{0.05}Rb_{0.5}Mo_3P_{.33}O_x$ | 343 | 92.2 | 58.4 | 60.4 |
| 47 | $Tl_{0.05}Rb_{0.5}Mo_3P_{.33}O_x$ | 316 | 87.4 | 56.2 | 61.2 |
| 48 | $K_{0.05}Rb_{0.5}Mo_3P_{.33}O_x$ | 343 | 86.4 | 62.4 | 70.1 |
| 49 | $K_{0.05}Rb_{0.5}Mo_3P_{.33}O_x$ | 329 | 83.4 | 60.2 | 72.2 |
| 50 | $Ca_{0.05}Rb_{0.5}Mo_3P_{.33}O_x$ | 343 | 84.9 | 54.1 | 61.8 |
| 51 | $V_{0.05}Rb_{0.5}Mo_3P_{.33}O_x$ | 343 | 81.4 | 61.4 | 76.2 |
| 52 | $V_{0.05}Rb_{0.5}Mo_3P_{.33}O_x$ | 371 | 90.2 | 66.2 | 74.0 |
| 53 | $Ce_{0.05}Rb_{0.5}Mo_3P_{.33}O_x$ | 343 | 82.6 | 48.8 | 56.7 |
| 54 | $W_{0.05}Rb_{0.5}Mo_3P_{.33}O_x$ | 343 | 82.7 | 56.9 | 68.2 |
| 55 | $W_{0.05}Rb_{0.5}Mo_3P_{.33}O_x$ | 357 | 90.2 | 62.4 | 67.7 |
| 56 | $Zr_{0.05}Rb_{0.5}Mo_3P_{.33}O_x$ | 343 | 93 | 59.8 | 64.3 |
| 57 | $Zr_{0.05}Rb_{0.5}Mo_3P_{.33}O_x$ | 316 | 77.7 | 53.6 | 68.7 |
| 58 | $Ba_{0.05}Rb_{0.5}Mo_3P_{.33}O_x$ | 343 | 84.4 | 55.0 | 62.6 |
| 59 | $Ba_{0.05}Rb_{0.5}Mo_3P_{.33}O_x$ | 316 | 70.2 | 47.2 | 65.4 |
| 60 | $Fe_{0.05}Rb_{0.5}Mo_3P_{.33}O_x$ | 343 | 92.8 | 59.1 | 60.0 |
| 61 | $Fe_{0.05}Rb_{0.5}Mo_3P_{.33}O_x$ | 316 | 90.6 | 62.1 | 66.6 |
| 62 | $Rh_{0.05}Rb_{0.5}Mo_3P_{.33}O_x$ | 343 | 90.1 | 57.4 | 63.5 |
| 63 | $Rh_{0.05}Rb_{0.5}Mo_3P_{.33}O_x$ | 316 | 77.8 | 63.9 | 82.1 |
| 64 | $Mn_{0.05}Rb_{0.5}Mo_3P_{.33}O_x$ | 343 | 97.4 | 64 | 65.7 |
| 65 | $Mn_{0.05}Rb_{0.5}Mo_3P_{.33}O_x$ | 329 | 96.1 | 68.2 | 72.3 |
| 66 | $Mn_{0.05}Rb_{0.5}Mo_3P_{.33}O_x$ | 316 | 87.7 | 63.3 | 72.2 |
| 67 | $Re_{0.05}Rb_{0.5}Mo_3P_{.33}O_x$ | 343 | 100 | 67.5 | 69.5 |
| 68 | $Re_{0.05}Rb_{0.5}Mo_3P_{.33}O_x$ | 329 | 96 | 62.1 | 64.8 |
| 69 | $Re_{0.05}Rb_{0.5}Mo_3P_{.33}O_x$ | 316 | 87 | 63.4 | 72.9 |
| 70 | $Ru_{0.05}Rb_{0.5}Mo_3P_{.33}O_x$ | 343 | 100 | 69.5 | 72.3 |
| 71 | $Ru_{0.05}Rb_{0.5}Mo_3P_{.33}O_x$ | 316 | 92.0 | 64.0 | 72.0 |
| 72 | $Ru_{0.05}Rb_{0.5}Mo_3P_{.33}$ | 288 | 52.4 | 31.3 | 57.5 |
| 73 | $Fe_{0.25}Sn_{0.025}Rb_{0.5}Mo_3P_{.33}O_x$ | 343 | 97.6 | 66.1 | 67.7 |
| 74 | $Fe_{0.25}Sn_{0.025}Rb_{0.5}Mo_3P_{.33}O_x$ | 329 | 95.0 | 67.3 | 69.8 |
| 75 | $Fe_{0.25}Sn_{0.025}Rb_{0.5}Mo_3P_{.33}O_x$ | 316 | 90.0 | 61.3 | 68.1 |
| 76 | $Fe_{0.025}Mn_{0.025}Rb_{0.5}Mo_3P_{.33}O_x$ | 343 | 94.9 | 63.8 | 65.2 |
| 77 | $Fe_{0.025}Mn_{0.025}Rb_{0.5}Mo_3P_{.33}O_x$ | 329 | 94.3 | 65.0 | 67.5 |
| 78 | $Fe_{.1}Mn_{.1}Rb_{0.5}Mo_3P_{.33}O_x$ | 343 | 93.1 | 63.9 | 66.6 |
| 79 | $Fe_{.1}Mn_{.1}Rb_{0.5}Mo_3P_{.33}O_x$ | 329 | 92.7 | 65.7 | 69.4 |
| 80 | $Fe_{.1}Mn_{.1}Rb_{0.5}Mo_3P_{.33}O_x$ | 316 | 85.9 | 61.8 | 70.5 |
| 81 | $Fe_{.1}Ni_{.1}Rb_{0.5}Mo_3P_{.33}O_x$ | 343 | 89.2 | 63.0 | 67.4 |
| 82 | $Fe_{.1}Ni_{.1}Rb_{0.5}Mo_3P_{.33}O_x$ | 329 | 88.8 | 59.7 | 65.2 |
| 83 | $Fe_{.1}Ni_{.1}Rb_{0.5}Mo_3P_{.33}O_x$ | 316 | 78.9 | 57.2 | 69.1 |
| 84 | $Fe_{.25}Mn_{.25}Rb_{0.5}Mo_3P_{.33}O_x$ | 329 | 89.2 | 58.2 | 65.2 |
| 85 | $Fe_{.25}Mn_{.25}Rb_{0.5}Mo_3P_{.33}O_x$ | 316 | 82.5 | 53.2 | 64.5 |
| 86 | $Sn_{0.25}Mn_{0.25}Rb_{0.5}Mo_3P_{.33}O_x$ | 329 | 91.7 | 57.1 | 70.6 |
| 87 | $Sn_{0.25}Mn_{0.25}Rb_{0.5}Mo_3P_{.33}O_x$ | 329 | 84.5 | 56.6 | 73.6 |
| 88 | $Sn_{0.25}Mn_{0.25}Rb_{0.5}Mo_3P_{.33}O_x$ | 343 | 88.6 | 56.2 | 71.2 |
| 89 | $Co_{0.25}Fe_{0.025}Rb_{0.5}Mo_3P_{.33}O_x$ | 343 | 90.7 | 63.8 | 67.0 |
| 90 | $Co_{0.25}Fe_{0.025}Rb_{0.5}Mo_3P_{.33}O_x$ | 329 | 85.0 | 61.7 | 68.8 |
| 91 | $Co_{0.25}Fe_{0.025}Rb_{0.5}Mo_3P_{.33}O_x$ | 316 | 76.0 | 56.0 | 70.9 |
| 92 | $Fe_{0.015}Sn_{0.035}Rb_{0.5}Mo_3P_{.33}O_x$ | 343 | 88.4 | 57.1 | 59.2 |
| 93 | $Fe_{0.015}Sn_{0.035}Rb_{0.5}Mo_3P_{.33}O_x$ | 329 | 96.4 | 67.4 | 69.9 |
| 94 | $Fe_{0.015}Sn_{0.035}Rb_{0.5}Mo_3P_{.33}O_x$ | 316 | 89.7 | 59.8 | 66.7 |
| 95 | $Fe_{0.035}Sn_{0.015}Rb_{0.5}Mo_3P_{.33}O_x$ | 343 | 97.3 | 62.8 | 64.5 |
| 96 | $Fe_{0.035}Sn_{0.015}Rb_{0.5}Mo_3P_{.33}O_x$ | 329 | 96.3 | 62.9 | 65.3 |
| 97 | $Fe_{0.035}Sn_{0.015}Rb_{0.5}Mo_3P_{.33}O_x$ | 316 | 92.0 | 63.2 | 68.6 |
| 98 | $Sn_{0.025}Ni_{0.025}Rb_{0.5}Mo_3P_{.33}O_x$ | 343 | 98.0 | 63.6 | 66.9 |
| 99 | $Sn_{0.025}Ni_{0.025}Rb_{0.5}Mo_3P_{.33}O_x$ | 316 | 88.7 | 59.8 | 70.9 |
| 100 | $Fe_{0.025}Mn_{0.025}Sn_{0.025}Rb_{0.5}Mo_3P_{.33}O_x$ | 343 | 91.5 | 58.0 | 60.9 |
| 101 | $Fe_{0.025}Mn_{0.025}Sn_{0.025}Rb_{0.5}Mo_3P_{.33}O_x$ | 329 | 92.4 | 60.0 | 63.1 |
| 102 | $Fe_{0.025}Mn_{0.025}Sn_{0.025}Rb_{0.5}Mo_3P_{.33}O_x$ | 316 | 88.8 | 56.9 | 61.6 |
| 103 | $Sn_{0.125}Cu_{0.5}$ | | | | |

TABLE-continued
PREPARATION OF METHACRYLIC ACID USING VARIOUS CATALYSTS OF THE INVENTION
Examples 34 to 103.

| Example | Catalyst | Reaction Temp. °C | Total Conversion | Single Pass Yield | Selectivity |
|---|---|---|---|---|---|
| | $Rb_{0.5}Mo_3P_{.33}O_x$ | 329 | 47.7 | 13.6 | 28.5 |

We claim:

1. The catalyst composition described by the formula $$A_aRb_bMo_3P_cO_x$$

wherein A is at least one element selected from the group consisting of arsenic, cadmium, indium, tin, thallium, potassium, calcium, vanadium, uranium, cerium, tungsten, nickel, zirconium, barium, iron, rhodium, manganese, rhenium, ruthenium, cobalt, and copper.
and wherein
   $a$ is a positive number less than about 20;
   $b$ is about 0.01 to about 3;
   $c$ is a positive number less than about 2;
   $x$ is the number of oxygens required by the valence states of the other elements present 2. The catalyst of claim 1 wherein A is at least one element selected from the group consisting of arsenic, cadmium, indium, thallium, and tin.

3. The catalyst of claim 1 wherein A is at least one element selected from the group consisting of potassium, calcium, vanadium, uranium, cerium, tungsten nickel, zirconium, barium iron, rhodium, tin, manganese, rhenium, ruthenium, cobalt and copper.

4. The catalyst of claim 1 wherein $a$ is a positive number less than about 12.

5. The catalyst of claim 1 wherein $b$ is about 0.01 to about 1.0.

6. The catalyst of claim 1 wherein $c$ is about 0.01 to about 0.75.

7. The catalyst of claim 1 wherein the catalyst is $In_{0.05}Rb_{0.5}Mo_3P_{0.33}O_x$.

8. The catalyst of claim 1 wherein the catalyst is $Ni_{0.05}Rb_{0.5}Mo_3P_{0.33}O_x$.

* * * * *